United States Patent [19]

Steiner et al.

[11] 4,242,194
[45] Dec. 30, 1980

[54] APPARATUS FOR SPECTROSCOPIC MEASUREMENT OF THE VELOCITY OF PARTICLES IN A FLUID

[76] Inventors: Rudolf Steiner, Muhltalerstr. 9, D-4000 Dusseldorf; Raimund Kaufmann, Florastr. 14, D-4005 Meerbusch-Buderich, both of Fed. Rep. of Germany

[21] Appl. No.: 98,371

[22] Filed: Nov. 28, 1979

[30] Foreign Application Priority Data

Dec. 7, 1978 [DE] Fed. Rep. of Germany ........ 2852978

[51] Int. Cl.$^3$ ............... G01N 27/26; G01N 27/28; G01N 33/16
[52] U.S. Cl. ............... 204/299 R; 204/180 R; 356/39; 356/344; 356/28; 356/337
[58] Field of Search ............... 204/299 R, 180 R; 356/27, 28, 28.5, 39, 40, 340, 344, 96, 103

[56] References Cited

U.S. PATENT DOCUMENTS

| | | | |
|---|---|---|---|
| 2,568,589 | 9/1951 | Labhart | 356/344 X |
| 3,552,855 | 1/1971 | Crossny et al. | 356/28 |
| 3,623,812 | 11/1971 | Hannig et al. | 356/344 |
| 3,708,402 | 1/1973 | Bean | 204/299 R |
| 3,732,014 | 5/1973 | Uzgiris | 356/344 X |
| 3,766,048 | 10/1973 | Flygare et al. | 204/299 R |
| 4,070,263 | 1/1978 | Treille et al. | 204/180 R |
| 4,097,153 | 6/1978 | DeRemigis | 356/103 |
| 4,101,220 | 7/1978 | Bean et al. | 356/344 |

FOREIGN PATENT DOCUMENTS

2086385 4/1971 France .

OTHER PUBLICATIONS

Vasilenko et al., "Laser Velocity Meters—A Comparative Study", *Optics and Laser Technology*, Dec. 1972, pp. 270-272.
DuBois et al., "Methode et Appareillage de Mesure Objective de la Mobilité des Spermatozoides Humains", Aim. Phys. Biol. et Med. (1975), 9 (1) pp. 19-41.
Mohan et al., "Laser Doppler Spectroscopy as Applied to Electrophoresis in Protein Solutions", Anal. Biochem., 70, pp. 506-525, (1976).
Smith et al., "Apparatus and Methods for Laser Doppler Electrophoresis", Contemp. Topics Analyt. Clin. Chem. 2, (1978), pp. 29-54.

*Primary Examiner*—Arthur C. Prescott
*Attorney, Agent, or Firm*—Marianne Rich

[57] ABSTRACT

In electrophoretic apparatus measuring the velocity of particles in a fluid, a reference beam and a scattered beam scattered by the particles in the fluid at various scattering angles must be heterodyned in order that the Doppler frequency shift resulting from the scattering by the moving particles can be determined. The previous need for adjusting the optical path of the reference beam so that is always impinges with the scattered beam, independent of the scattering angle, upon the mixer or heterodyner is avoided by an automatic control of the direction of the reference and scattered beams relative to the mixer so that they both always impinge upon a predetermined location in the mixer independent of the scattering angle. The construction of the measuring cell and ways of mounting same in a housing to allow easy refilling and replacement are also disclosed.

36 Claims, 8 Drawing Figures

APPARATUS FOR SPECTROSCOPIC MEASUREMENT OF THE VELOCITY OF PARTICLES IN A FLUID

CROSS REFERENCE TO RELATED APPLICATIONS AND PUBLICATIONS

U.S. Pat. No. 3,766,048; (Flygare et al.).

U.S. Pat. No. 3,708,402; (C. P. Bean).

"Laser Doppler Spectroscopy as Applied To Electrophoresis in Protein Solutions", R. Mohan, R. Steiner, and R. Kaufmann, *Analytical Biochemistry* 70, 506–525, 1976.

The present invention relates to electrophoretic measuring apparatus and, more particularly, to apparatus wherein the velocity of particles in a fluid is measured spectroscopically by measuring the Doppler shift in frequency of an electromagnetic wave scattered by the moving particles.

BACKGROUND AND PRIOR ART

In known apparatus of this type, a source of substantially monochromatic coherent electromagnetic radiation is provided, as is a measuring cell holding the fluid in which the particles are contained. The electromagnetic radiation is split into a measuring beam passing through the measuring cell and the reference beam. The movement of the particles in the fluid under the influence of an applied electric field causes the electromagnetic energy in the measuring beam to be scattered. The radiation scattered at a selected angle to the incoming measuring beam is then heterodyned with the reference beam and the resulting beat frequency is evaluated to determine the Doppler shift of the measuring beam frequency due to the scattering by the moving particles.

When a laser is used as the source of electromagnetic radiation, the above described apparatus allows a relatively rapid and objective measuring of the velocity of particles such as proteins or cells within a fluid. This type of measurement is particularly important in the diagonstic field and is used, for example, to determine the electrophoretic mobility of erythrocytes and leukocytes as well as their sedimentation speed. It can also be used to measure the mobility of sperm.

When the particles in the fluid are weakly scattering particles, the radiation emanating from the glass walls of the measuring cells may be used as the reference beam. For strongly scattering particles, a definite reference beam must be introduced, since the radiation from the glass walls is no longer sufficient.

All the known apparatus of this type has the disadvantage that different measuring angles, i.e., different angles between the incident measuring beam and the selected scattered beam require a new adjustment of the optical components determining the path of the reference beam, so that the scattered and measuring beams will fall on the same location in the mixer where the heterodyning is carried out. Since a series of many measurements must often be carried out in order to obtain information about the type and structure of the scattering particles, a great deal of time is lost in this adjustment of the referenced beam.

SUMMARY OF THE INVENTION

It is an object of the present invention to furnish apparatus of the above described type in which the referenced and scattered beams always fall unto the same location in the mixer, regardless of the scattering angle at which the measuring is being taken.

In accordance with the invention, in a system of the above described type, means are provided wherein at least one of the beams (reference beam or scattered beam) is deviated so that, independent of the scattering angle at which the measurement is being taken, both beams fall on the same location in the mixer.

In a preferred embodiment, the beam which is so deviated is the scattered beam. For this purpose, a convex lens is arranged in the path of the radiation between the measuring cell and the mixer so that its focal point lies within the measuring cell. These scattered beams leave the convex lens in a direction parallel to the optical axis of the lens. An optical select element is then provided on which the beams emanating from the convex lens impinge. The optical selector element (e.g. a deviating prism) deviates the beam incident thereon in a direction towards the desired location in the mixer. A selection of the scattering or measuring angle at which the measurement is to be carried out is achieved only by relative linear movement between the convex lens and the measuring cell on the one hand and the incident side of the optical selector element on the other hand. The remaining elements in the apparatus including the laser beam source, the beam splitter, the beam mixer, and the detector connected to the mixer output all remain in the same position, regardless of the angle at which the scattered beam is being measured. The required linear movement between the convex lens and the measuring cell and the optical selector element can be carried out very rapidly and with great accuracy.

A pin diaphragm may be arranged in the path of the selected scattered beam. Since it is also desirable to concentrate the incident measuring beam on as small a scattering volume within the measuring cell as possible, a second convex lens is arranged in the path of the beam between the beam splitter and the measuring cell so that its focal point coincides with the focal point of the first convex lens. It must be understood of course that when a convex lens is mentioned, any optical system which has the properties of converging the rays at a focal point could be substituted.

When the scattering or measuring angle is changed, the direction of the scattering vector also changes. For theoretical reasons it is desirable that the scattering vector always points in the direction of movement of the particles. This is accomplished in simple fashion by causing the angle of incidence of the measuring beam upon the measuring cell to change as the measuring angle is changed. For this purpose, a second optical selector element is provided which is interposed between the beam splitter and the second convex lens, the position of the second optical selector element relative to the second convex lens being adjustable. If the first and second optical selector elements are moved simultaneously and by the same amount relative to the first and second convex lens, the scattering vector will maintain the same position throughout. Preferably, both convex lenses and the two optical selectors are identical to each other and are arranged with mirror symmetry relative to a central plane which is perpendicular to the optical axis of the convex lenses and passes through the measuring cell. The two optical selector elements or prisms may be mounted on the same carriage, the carriage being movable by means of a calibrated drive in a direction perpendicular to the optical axis of the two lenses. Similarly, the prisms could remain in the fixed position while the convex lenses and the measuring cell are moved relative thereto, i.e., are also arranged on a carriage wich is movable by the same type of drive.

The above described equipment allows measurement of the velocity of particles whose direction of movement is parallel to the direction in which the prisms may be moved relative to the lenses. It is, for some applications, required that the same test samples be used to measure not only the electrophoretic mobility but also the sedimentation rate of the particles, the first measurement being concerned with a particle movement in a horizontal plane while the second is concerned with a particle movement in the vertical plane. Where it is desired that both measurements be carried out on a sample without requiring changes or adjustments in the general structure or in the optical elements, an adjustment is provided for moving the convex cell and the measuring cell jointly in a direction perpendicular to the direction in which the position of the prisms is adjusted. If the equipment is so arranged that the first adjustment direction is the horizontal plane, then the selector elements are so arranged that the beam incident unto the measuring cell and the selected scattered beam lie in a vertical plane containing the optical axis of the two lenses. Then the scattering vector always points in the vertical direction regardless of the adjustment of the measuring cell and the convex lenses in the vertical direction, so that under these conditions the sedimentation rate of the particles may be measured.

In a particularly preferred embodiment, the measuring cell is cylindrical and the cylinder axis extends horizontally in a direction perpendicular to the optical axis of the convex lenses. Such a measuring cell can be a capillary glass tube, if care is taken that the outer radius of the capillary remains constant. If now the optical selector elements are so arranged that the measuring beam passes through both convex lenses along the optical axis thereof, then measurements at different scatering angles may be carried out while maintaining the direction of the scattering vector if the measuring cell is moved in the vertical direction. If the cylinder axis of the measuring cell intersect the optical axis of the convex lens, then the measuring beam will impinge radially unto the measuring cell and will pass through the latter in a straight line. If, the measuring cell is moved in the vertical direction from this position either upwards or downwards, then the measuring beam no longer impinges perpendicularly unto the outer wall of the measuring cell and therefore is diffracted. Experiments have shown that when all other variables remain constant, the scattering angle is proportional to the displacement of the measuring cell in the vertical direction, this displacement being measured from a horizontal plane containing the cylinder axis. This proportionality holds to a good approximation up to scattering angles of approximately 20°. So constructed measuring apparatus thus allows vertical or horizontal movement of the particles to be detected by, respectively, linear movement of the measuring cell or linear movement of the optical selector elements, without requiring any change in the construction of the apparatus.

The apparatus further can be constructed in a very compact manner and is easy to service, so that a great number of measurements can be conducted in a very short time. In particular, the complicated adjustment of the reference beam required for carrying out a series of angle-dependent measurements in conventional equipment is avoided. However, the above described equipment allows measurements to be carried out up to, at the most, a measurement angle of 60°.

It is a further object of the present invention to furnish equipment wherein measurements can be carried out at scattering angles exceding 60°. For this purpose, the beam mixer and the detector are mounted on a carrier which is rotatable around an axis of rotation passing through the measuring cell. By rotating the carrier, measurements can be carried out for scattering angles up to approximately 180°. It is desired that no adjustment of the optical elements of the reference beam be required. Therefore, the reference beam may travel through a flexible wave guide over at least a part of its path. For example, the reference beam, after leaving the beam splitter may be applied to a monomode optical fiber whose output end is fixedly arranged relative to the beam mixer. The reference beam will thus impinge unto the same location in the mixer regardless of the position of the rotatable carrier and will always be mixed in the beam mixer with the selected scattered beam. Preferably, the length of the flexible wave guide is such that the total length of path travelled by the reference beam is equal to the total length of path of the measuring beam. This is important to allow full utilization of the coherent length of the laser.

In an alternate preferred embodiment, the reference beam and the incident measuring beam lie in the same plane, as do the reference beam and the scattered measuring beam.

A scattering element is provided where the reference beam crosses the axis of rotation of the carrier. The scattering element scatters the reference beam over an angle at least as large as the angle through which the carrier may be rotated. Under these conditions, a deviating prism for either the measuring beam or the reference beam may be fixedly mounted on the carrier in a predetermined spatial relationship to the beam mixer. As the carrier is rotated, the scattered beam at the selected measuring angle and a part of the reference beam scattered at the same angle will be detected and will fall on the same location in the mixer, regardless of the measuring angle. The optical elements are preferably so placed on the carrier that the path length for the reference beam and the measuring beam are equal.

The scattering element for the reference beam can be a cylindrical glass capillary arranged co-axially with the axis of rotation or it may be the tip of a needle also arranged co-axially to the axis of rotation. When only the carrier with the beam mixer and the receiver are rotated, the direction of the scattering vector will change as a function of the measuring angle. To maintain the scattering vector in the direction parallel to the direction of the movement of the particles, means may be provided which rotate the measuring cell around the axis of rotation by an angle equal to half the angle of rotation of the mixer.

The carrier may be a disc wich is rotatably mounted on a table on which the source of radiation, the beam splitter and the measuring cell are also mounted. An angle measuring arrangement for measuring the angle of rotation of the disc relative to a predetermined reference position must be provided. The measuring cell may also be mounted rotatably relative to the table, suitable gearing being provided so that rotation of the disc causes rotation of the measuring cell by one half of the angle through which the disc is rotated.

It is a further object of the present invention to furnish a measuring cell which is constructed and mounted in such a way that fluid samples can readily be replaced and that the measurement of electrophoretic mobility of the particles and of their sedimentation rate can be carried out readily. In a preferred embodiment, the measuring cell is constituted by a pipe having two open ends and is mounted in a cell holder which also has a through channel for the measurement beam. The position of the pipe may be changed from the first position which is a refill and cleaning position in which the open ends of the pipe are aligned with an inlet and an outlet in the housing, and the measuring position in which the connection between the measuring cell and the outer atmosphere is broken.

In a preferred embodiment, the cell holder is a cylindrical body which has a diametral hole for receiving the measuring cell and an axial through channel for the measuring beam. The housing has a block with a cylindrical through bore which has an inside diameter corresponding to the outer diameter of the cell holder, the inlet and outlet openings being bores situated diametrically opposite each other in the block. A simple rotation of the cell holder allows the open end of the pipe constituting the measuring cell to be aligned with the inlet and outlet openings so that the cell may be washed out and refilled. When the cell has been refilled, the cell holder is again turned so that the connection between the inlet and outlet openings and the cylindrical measuring cell is broken. As the cell holder is pulled out of the bore, the measuring cell can readily be replaced by another.

This type of arrangement of the measuring cell also allows an electric field to be applied to the sample, such as is necessary in order to measure the electrophoretic mobility of the particles. For this purpose, two chambers are provided in the housing, arranged on each side of the block, diametrically opposite one another relative to the axis of the bore receiving the cell holder. Each chamber contains a buffer fluid and an electrode. The receiving bore for the cell holder is connected to the two chambers by openings in the block which are set off in the peripheral direction relative to the inlet and outlet openings and sealed by semipermeable membranes. In the measuring position, the axis of the measuring cell is aligned with the line connecting the two openings, so that the two semipermeable membranes abut the opened ends of the measuring cell or the openings in the cell holder receiving the measuring cell. When the electrodes in the chambers are connected to a voltage source, current can flow through the buffer fluid, the membranes and the fluid sample. Preferably, the electrodes are mounted in electrode holders which in turn are detachably connected to the housing, so that replacement or cleaning of the electrodes is facilitated. The electrode holders may, for example, be screwed into a bore in the wall of the housing and may carry the electrodes at the inner end which projects into the chamber. Each electrode is electrically connected to a terminal on a part of the electrode holder lying outside of the particular chamber. The housing is of course constructed of a non-conductive material, preferably a plastic. The membranes also are mounted in such a way that they can be replaced in a simple fashion but still offer a sufficient seal between the chambers and the receiving bore for the cell holder. A cylindrical contact surface for the membrane is therefore provided near the opening in the wall of the block facing each of the chambers. The surface lines of the cylinders extend in the direction perpendicular to the cylinder axis of the receiving bore and intersect the cylindrical wall of the bore. Further, a membrane holder with a cylindrical clamping surface matched to the above mentioned contact surface and having a through channel aligned with the opening is provided, the membrane holder being pressed against the contact surface by a clamping arrangement. The openings in the block are thus generated by an intersection of the cylindrical outer surface of the receiving bore with the cylindrical contact surface. Thus on the one hand a very tight seal can be formed between each of the chambers holding the buffer solution and the receiving bore while at the same time a membrane is so tightly pressed against the top surface of the cylindrical cell holder, that no fluid can escape through the opening of the bore receiving the measuring cell.

The clamping arrangement preferably consists of a bushing having an internal thread and a hollow screw which may be screwed into the bushing and which has an axial bore. One side of the arrangement is braced against the membrane holder and the other side is braced against the wall of the chamber opposite the contact surface. Current can flow through a channel formed inside the bushing and the hollow screw.

DRAWINGS ILLUSTRATING PREFERRED EMBODIMENT

DESCRIPTION OF THE PREFERRED EMBODIMENT

Figure 1:
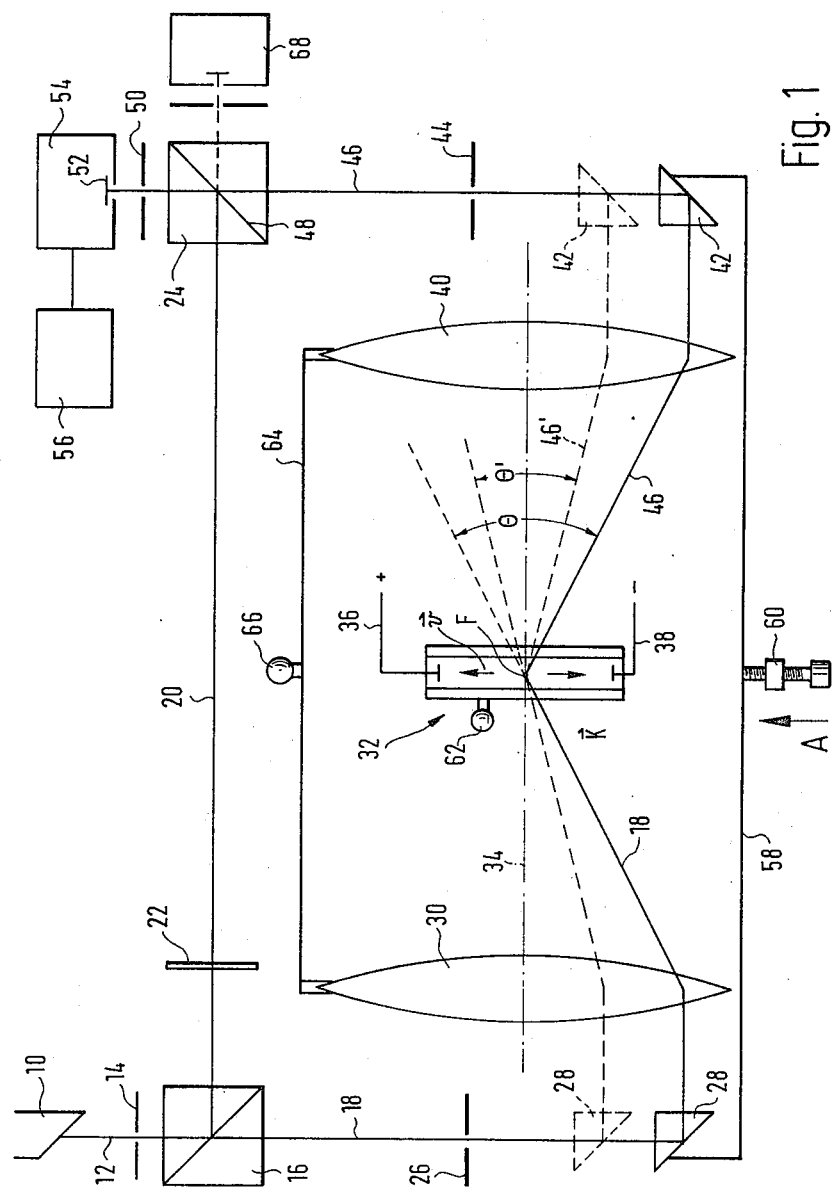
FIG. 1 is a schematic top view of the first embodiment of the measuring arrangement of the present invention.

The measuring arrangement shown in FIG. 1 includes a laser 10 which constitutes a source of monochromatic coherent electromagnetic radiation. The light beam 12 emitted by laser 10 passes through a pin diaphragm 14 to a beam splitter 16. Beam splitter 16 divides beam 12 into two beams of equal energy content, namely a measuring beam 18 and a reference beam 20. Of course the energy applied to the beam splitter could be apportioned differently between the measuring and reference beams. In the illustrated example, beam splitter 16 is made up of two right angle prisms. Other suitable beam splitters could of course be substituted.

The intensity of the reference beam is controlled by a rotatable polarizer 22. After passing through polarizer 22, beam 20 impinges upon a mixer 24 which is constructed in identical fashion to beam splitter 16.

Measuring beam 18 passes through a pin diaphragm 26 and a deviating element, here illustrated as a right angle prism, 28. The beam is deviated by 90 degrees from its original direction of propagation and impinges upon a biconvex lens 30 in a direction parallel to the optical axis of the latter. A cylindrical measuring cell 32 is arranged at the focal point of lens 30. The cylinder axis is perpendicular to the optical axis 34 of lens 30 and extends in the direction parallel to the direction of beam 12. Measuring cell 32 contains the test particles which will move in the direction parallel to the cylinder axis under the influence of a voltage applied to electrodes 36 and 38.

A biconvex lens 40, a right angle prism 42, and a pin diaphragm 44, respectively identical to lens 30 prism 28 and pin diaphragm 26, are arranged on the side of measuring cell 32 facing away from lens 30. Specifically, they are so arranged as to form the mirror image of these elements relative to a plane passing through the cylinder axis of the measuring cell in a direction perpendicular to the plane of the paper.

Measuring beam 18 after deviation by prism 28 is again deviated by lens 30 in a direction towards its optical axis. It passes through the common focal point F of lenses 30 and 40. Measuring beam 18 is scattered by the particles moving in measuring cell 32, the frequency of the scattered light being shifted by the Doppler effect because of the movement of the scattering particles. The scattered light emanating from the measuring cell in the vicinity of the focal point F falls on lens 40 and emerges from lens 40 in a direction parallel to the optical axis 34. The part of the light beam emerging from lens 40 which falls on prism 42 is deviated by 90 degrees towards pin diaphragm 44. Beam 46 emerging from diaphragm 54 falls onto beam mixer 24 in such a way that it, together with reference beam 20 whose direction of propagation was changed at the diagonal surface 48 of beam mixer 24, pass through a pin diaphragm 50 and fall on the photocathode 52 of a detector 54. Since the frequency of the scattered beam 46 differs slightly from the frequency of reference beam 20, detector 54 receives a signal whose amplitude is modulated by the beat frequency. This signal is used to derive the frequency spectrum from which can then be derived the Doppler frequency shift and therefrom the velocity of the moving particles. Evaluation stage 56 in which these computations are carried out is not illustrated in detail since it is a known unit and since the present invention is not concerned with this evaluation, but rather with a particularly simple way of causing the correct signal to fall on photocathode 52, without adjustment of reference beam 20, regardless of the scattering angle through which the measurement is being taken.

The light from measuring beam 18 which enters measuring cell 32 is, in principle, scattered in all directions. The scattering takes place in the main in the forward direction when the particles are larger than the wave lengths of the impinging laser beam. In order to determine the Doppler frequency shift resulting from the scattering by the moving particles of the light falling into measuring cell 32, a knowledge of the scattering angle and the scattering vector is required. Scattering angle θ is the angle between the direction of the incoming beam and the direction of the particular scattered beam being observed, that is the angle between the incoming beam and the direction relative to the incoming beam at which the scattering volume is being observed. The scattering angle thus also constitutes the measuring angle. In FIG. 1 the angle θ between the direction of measuring beam 18 and the selected scattered beam 46 is illustrated.

The scattering vector K results from the difference between the wave vector of the impinging wave and the wave vector of the scattered wave. The reasons which will be explained in greater detail below, the direction of scattering vector K is in the direction of the cylinder axis of measuring cell 32 in the arrangement illustrated in FIG. 1.

If it is now desired to carry out a series of measurements at different scattering angles, this can be done in a very simple way with the arrangement illustrated in FIG. 1. Specifically, it is only necessary that prism 42 be shifted in the direction towards beam mixer 24. If prism 42 is moved from the position shown in FIG. 1 in solid lines to the position shown in broken lines, then a scattered beam 46' having a smaller scattering angle θ' will be detected. However, this changed position of prism 42 does not result in any change in either the direction or the position of the measuring beam coming from prism 42. The latter thus always impinges upon beam mixer 24 in the same location. It thus always combines properly with reference beam 20 without necessitating any change in the reference beam location or direction for a change in measuring angle. Prism 42 and diaphragm 44 thus constitute an optical arrangement which allows selection of light scattered at a particular measuring angle for measuring purposes.

Reference to FIG. 1 will show that prism 28 which deviates measuring beam 18 towards lens 30 is also adjustable in position, namely in the direction of the propagation of laser beam 12. Specifically, prisms 48 and 42 are both fastened on to a carriage 58 which may be moved by a schematically illustrated calibrated fine control 60. Therefore prisms 28 and 42 are always moved by an identical distance, as is indicated by the positions of the prisms shown by the broken lines. Because of this symmetrical arrangement and symmetrical movement of prisms 28 and 42, the scattering vector K always points in the direction of the cylinder axis of measuring cell 32 and is therefore always parallel to the velocity vector v which indicates the velocity of the particles in measuring cell 32. If measuring beam 18 would always impinge in the same direction onto measuring cell 32, then, for different scattering angles θ, the scattering vector would change its direction by an amount θ/2.

Figure 7:
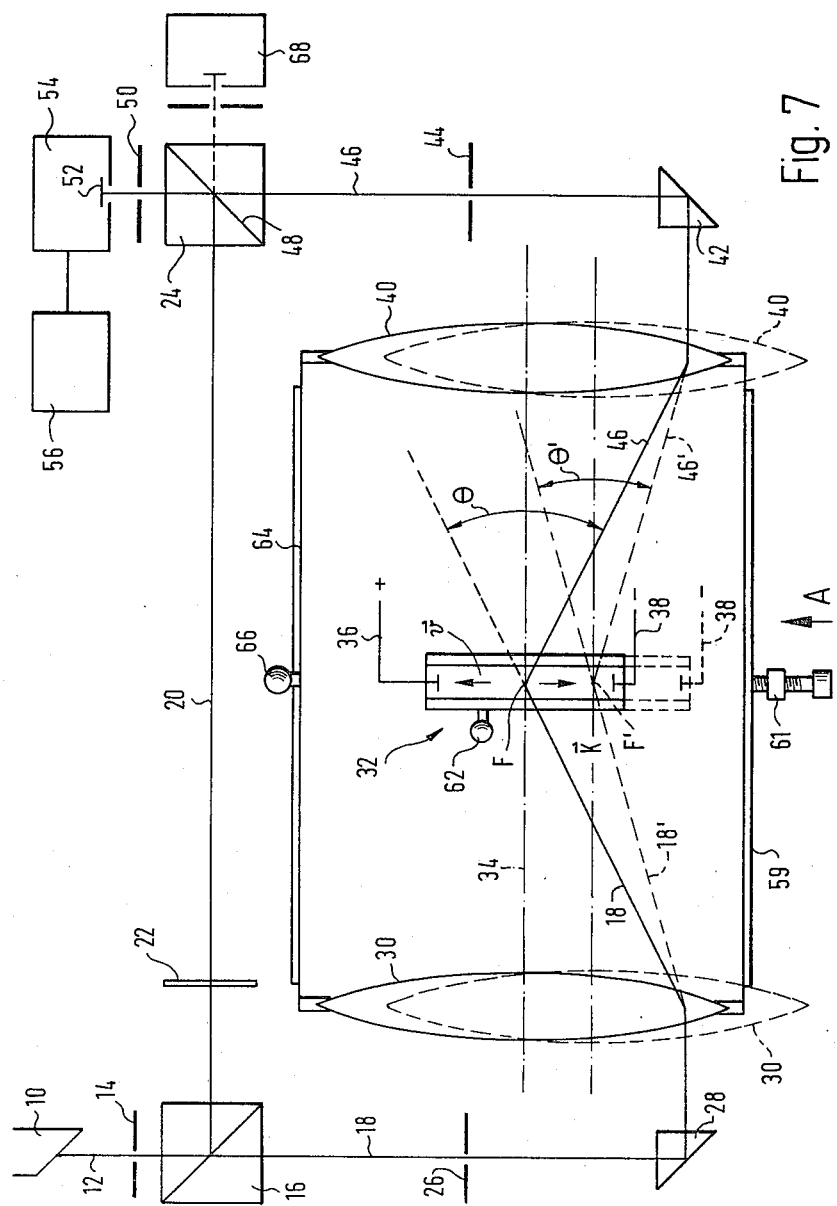
FIG. 7 is a variation of the embodiment of the present invention illustrated in FIG. 1.

It must be stressed again, that laser 10, beam splitter 16, beam mixer 24, detector 54, measuring cell 32 and lenses 30 and 40 remain in the same position throughout the whole measuring series. A change in the measuring angle is effected solely by moving the carriage 58 with prisms 28 and 42. Therefore, in order to carry out a whole measuring series for different measuring (scattering) angles, it is only necessary to move drive 60, which is a calibrated drive, by an amount required for the particular desired angular change. A change in the direction or position of the reference beam and therefore an adjustment of the optical elements determining the path of the reference beam is not required. This results in a considerable shortening of the time required for carrying out this series of measurements. FIG. 7 shows a variation of the arrangement shown in FIG. 1. Corresponding elements are labelled with the same reference numerals. The difference between the embodiment shown in FIG. 7 and that shown in FIG. 1 is, that in FIG. 7 prisms 28 and 42 are mounted in a fixed position, while lenses 30 and 40 together with measuring cell 32 are mounted on a carriage 59. Carriage 59 is movable by a fine drive 61 in a direction parallel to the direction of propagation of beams 18 and 46. If the carriage with lenses 30 and 40 and measuring cell 32 is moved from the position shown in solid lines to that indicated by broken lines, a beam 46' with a scattering angle $\theta'$ will fall onto prism 42 instead of beam 46 with scattering angle $\theta$. This arrangement has the advantage that the carriage 59 carrying the lenses and the measuring cell is smaller than the carriage 58 which carries prisms 28 and 42 as shown in FIG. 1.

Figure 2:
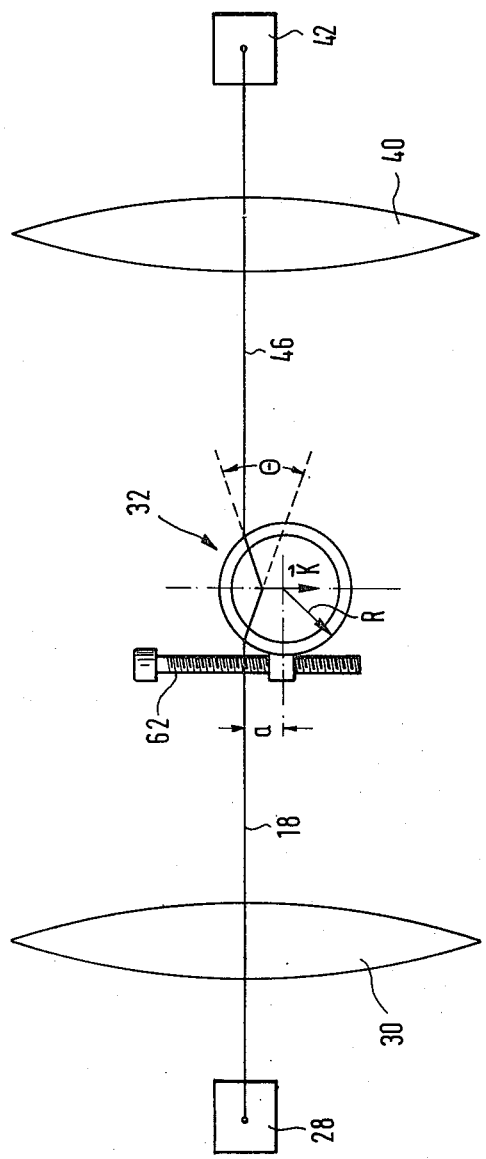
FIG. 2 is a schematic view of the equipment shown in FIG. 1 in the direction of arrow A.

The arrangement shown in FIGS. 1 and 7 allow measurement of movement of particles in the horizontal direction, as is for example required in the measuring of electrophoretic mobility of the particles. It is however also possible with the apparatus of the present invention to measure the sedimentation rate of the particles, that is the speed with which the particles move in the test fluid under the influence of gravity. For example, the blood sedimentation rate may be measured. This is a clinically important parameter. In order to conduct an angle-dependent measurement of a vertical velocity, prisms 28 and 42 (FIG. 1) or lenses 30 and 40 (FIG. 7) are moved so that the beam coming from prism 28 and the beam entering prism 42 propagate along the optical axis of lenses 30 and 40. In order to have a vertical scattering angle and to change the scattering angle, the cylindrical measuring cell whose axis in the arrangement shown in FIG. 1 is in the same plane as the optical axis of lenses 30 and 40 is shifted in the vertical direction as shown in FIG. 2. Under these conditions the measuring beam 18 does not pass through the cylindrical measuring cell in a straight line, but rather the path of propagation shown in FIG. 2 results. If a denotes the vertical movement of the measuring cell from its original position, R denotes the outer radius of the measuring cell and n denotes the index of refraction of the glass wall of the measuring cell, then, if it is assumed that the index of refraction of the glass wall is approximately equal to the index of refraction of the test fluid, the following equation will be a good approximation:

$$\sin \frac{\theta}{2} \approx \frac{a}{R} \left( \frac{n-1}{n} \right) \left( 1 + \frac{a^2}{2nR^2} \right)$$

From this equation it is seen that up to an angle $\theta$ of approximately 20°, the scattering angle $\theta$ is proportional to the change in position a. Thus measuring cell 32 is mounted in such a way that it can be shifted in the vertical direction by the aid of a calibrated drive 62, schematically indicated in FIG. 2. It is necessary for this type of measurement that the outer radius R of the measuring cell is constant throughout.

If a measuring cell with plane parallel surfaces is used instead of cylindrical measuring cell 32, a vertical scattering vector can be created by mounting lenses 30 and 40 as well as the measuring cell in such a way that their position in the vertical direction can be changed together. For this purpose lenses 30 and 40 and the holder for the measuring cell are arranged on a table 64 which is movable in the vertical direction by means of a fine drive 66. In FIG. 1 a second detector 68 is arranged at right angles to detector 54. The two detectors may be operated in parallel, or may be used to analyze the polarized and unpolarized components of the scattered light simultaneously by use of polarizers at 90° angles relative to each other. Such an arrangement is important for the measurement of anisotropic molecules or particles.

The main advantage of the above described apparatus is thus that a change in the measuring angle is achieved either by a linear movement of prisms 28 and 42 relative to lenses 30,40 or a linear movement of measuring cell 32. All other units of the apparatus remain fixed and calibrated as originally set. No goniometer is required. It is true that for the arrangement shown in FIG. 1 scattering a angle $\theta$ of at the most 60° can be measured. Apparatus in which measuring of larger scattering angles is also possible will now be described with reference to FIGS. 3 and 4.

Figure 3:
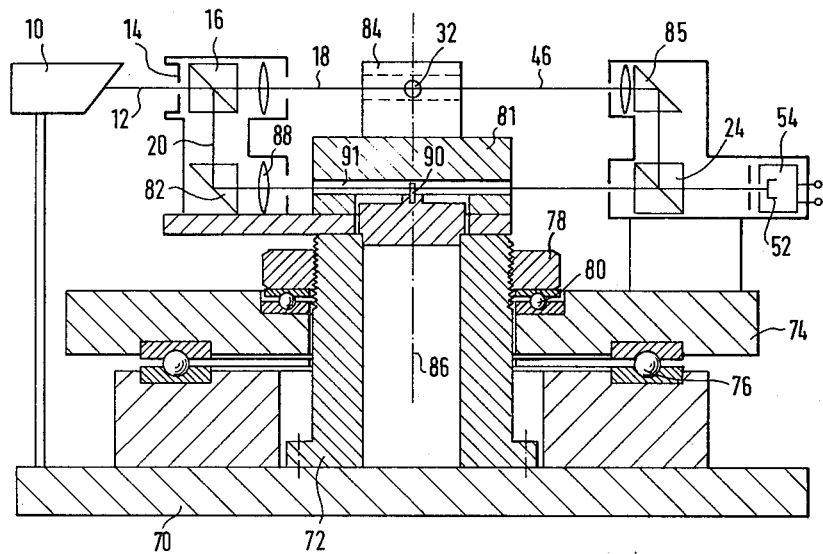
FIG. 3 is a partially sectional schematic side view of the second embodiment of a measuring arrangement according to the present invention.

In FIG. 3 a central column 72 is screwed on to a table 70. Also mounted on table 70, coaxially to central column 72 and on a ball bearing 76, is a disc 74. Disc 74 is maintained in a fixed position in the axial direction of central column 72 by a nut 78, a further ball bearing 80 being arranged between nut 78 and disc 74.

In this arrangement laser 10, diaphragm 14, beam splitter 16 and a deviating prism 82 for reference beam 20 are mounted fixedly on table 72. A measuring cell arrangement including measuring cell 32 is mounted at the upper end of column 72. The measuring cell is made of a thin glass tube whose axis is arranged intersecting the axis of rotation 86 of disc 74 at right angles. Detector 54, beam mixer 24 and a deviating prism 85 for the scattered measuring beam 46 are arranged on disc 74. The detector can thus be rotated around axis 86 jointly with the beam mixer, in order to intercept scattered beams at different scattering angles. In conventional arrangements of this type it is necessary to adjust the position of the reference beam in accordance with the rotational position of the above mentioned elements, that is the optical elements which determined the direction of propagation of the reference beam have to be adjusted. The need for this adjustment is avoided in the present invention. Specifically, reference beam 20 emerging from beam splitter 16 is deviated by a prism 82 and is focused by lens 88 onto a glass capillary tube 90. Capillary tube 90 is mounted coaxially to the axis of rotation 86. The reference beam is scattered by the capillary tube. Specifically, propagation of reference beam 20 takes place in a slit 91 which extends in the horizontal direction over half the cross-section of surface of column 72. As is particularly clearly shown in FIG. 4, at the input side of measuring cell 32 measuring beam 18 and reference beam 20 are in a vertical plane containing the axis of rotation 86. Similarly, the scattered beam 46 and reference beam 20 at the output side of measuring cell 32 are in a vertical plane containing axis 36. However, the latter plane is rotated relative to the first mentioned plane by the scattering angle $\theta$. The two planes therefore intersect along axis 86. Since scattering of the reference beam takes place at the point of intersection of the reference beam with axis 86, a scattered part of reference beam 20 will fall on beam mixer 24 regardless of scattering angle $\theta$. That means that no optical element determining the direction of propagation of the reference beam need be readjusted or recalibrated when disc 74 turns. The reference beam and the desired measuring beam always fall on the same point of beam mixer 24, independent of the selected measuring angle $\theta$ and from there impinge upon detector 54 in a direction independent of the angle of rotation of the disc. It is obvious that with this arrangement measurements at scattering angles of more than 90° can readily be carried out.

If the scattering vector K is to remain parallel at all times to the direction of movement of the particles, measuring cell 32 must be turned by an angle $\theta/2$ when the disc is turned by an angle $\theta$. This requirement can be met without difficulty by use of gearing having a suitable gear ratio between the disc and a mounting for the measuring arrangement 84. Adjustment of the position of measuring arrangement 84 on the column can be achieved by two carriages 81 arranged at right angles to each other.

Figure 4:
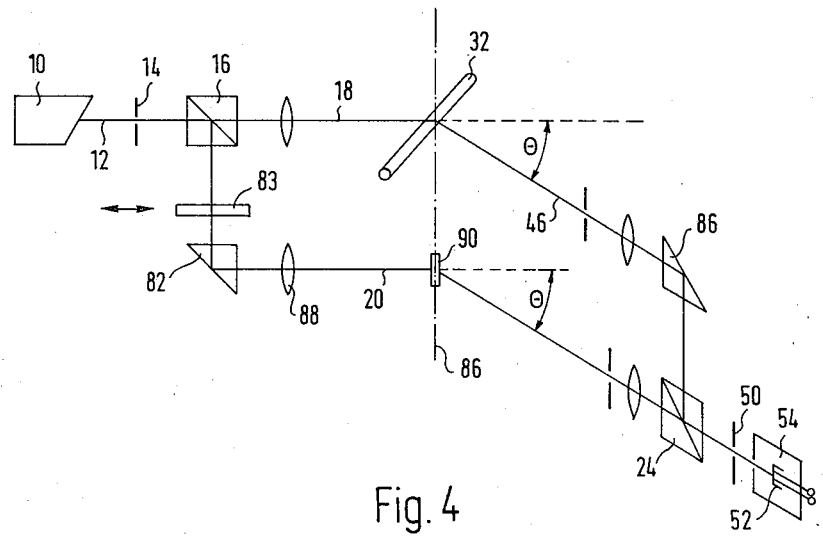
FIG. 4 is a perspective schematic diagram showing the directions of propagation of beams in the arrangement shown in FIG. 3.

It is a particular advantage of the arrangement according to FIGS. 3 and 4 that the optical paths for the measuring and reference beam are exactly identical because of prisms 82 and 85 and beam splitter 16 and beam mixer 24. This allows optimum use of the length of coherence of the laser beam. This is not the case with the arrangement shown in FIGS. 1 and 2. However, even the latter arrangement can be so compactly built that the difference in the path length between the measuring beam and the reference beam is relatively small and that, for a length of coherence for the laser beam of several meters, no serious difficulties arise.

It is also to be noted that a grey filter 83 is arranged in the path between beam splitter 16 and deviating prism 82 so that the intensity of the reference beam may be varied.

Instead of scattering the reference beams by means of capillary tube 90, the reference beam could be applied to beam mixer 24 by means of optical fibers. Since the optical fibers are very flexible it is again possible to rotate disc 74 without requiring a further adjustment of the path of the reference beam. If optical fibers are used the additional advantage results that the length of path of the reference and measuring beams can be adjusted to be exactly equal.

In FIGS. 1 through 4 the measuring cell is schematically pictured as a tube. A particular arrangement for mounting the measuring cell will now be described relative to FIGS. 5 and 6. This arrangement allows the electrophoretic velocity of the particles to be measured very easily and also allows a quick and convenient changing of the test samples.

Figure 5:
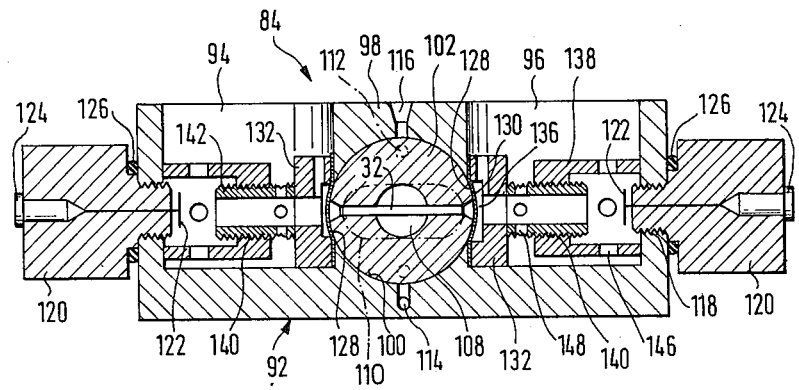
FIG. 5 is a sectional view for a measuring cell arrangement suitable for measuring the velocity of particles moving under the influence of an electric field.
Figure 6:
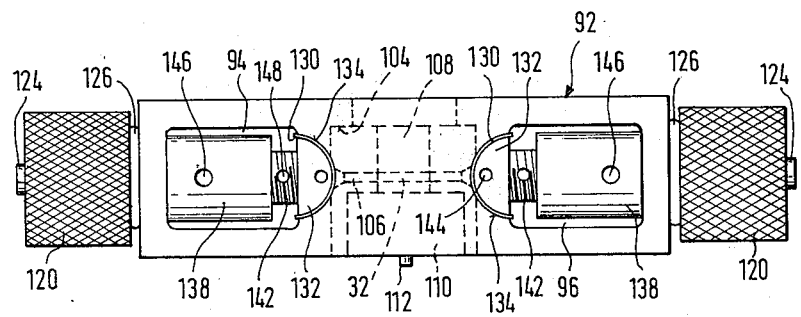
FIG. 6 is a top view of the measuring equipment shown in FIG. 5.

Referring now to FIGS. 5 and 6, a housing 92 is shown which is in the form of a right parallelepiped. Housing 92 has two open chambers 94 and 96 which are separated by a block 98 from each other. Block 98 has a cylindrical bore 100 for receiving a cylindrical cell holder 102. Bore 100 extends through the whole block 98, but has a shoulder 104 against which one face of cell holder 102 abuts, so that the latter is exactly positioned in the axial direction within bore 100.

Cell holder 102 also has a radial bore 106 which extends in the direction perpendicular to the cylinder axis. Bore 106 receives measuring cell 32, which is a capillary glass tube. Bore 106 has a conical shape at its radial extremities. Cell holder 102 further has an axial hole which is constituted by a bore 108 which is continued by an oblong reamed hole 110. Bore 108 faces the incident measuring beam, while opening 110 is on the side of the scattered measuring beams. Reamed hole 110 increases the angle and thereby the possible measuring region which may be scanned without adjustment of housing 92. Two pins 112 are arranged diametrically opposite one another at the outer surface of cell holder 102. A key applied to pin 112 allows the cell holder to be turned within bore 100. Turning of cell holder 102 within bore 100 allows measuring cell 32 in its vertical position to be aligned with a lower inlet channel 114 and an upper outlet channel 116 within block 98. Both of channels 114 and 116 are widened in a conical shape towards the outside, to allow application of a syringe.

If it is desired to replace measuring cell 32, cell holder 102 may be pushed out of bore 100.

Each of the walls of housing 92 away from block 98 has a threaded hole 118 whose axis extends through measuring cell 32 when the latter is turned in the horizontal direction. Electrode holders 120, each carrying an electrode 122 at its inner extremity, can be screwed into threaded holes 118. Each electrode holder 120 consists of a cylindrical knob which has a knurled outer surface. A socket 124 is arranged on the side of electrode holder 12 which is away from the electrode, and is electrically connected to the latter through electrode holder 120. When electrode holder 120 is screwed into bore 118, a ring shaped seal 126 is inserted between the wall of the housing and electrode holder 120. This prevents buffer fluid from escaping from chambers 94 and 96.

As shown in FIG. 6, the walls of chambers 94 and 96 adjacent to block 98 are of cylindrical shape, the axis of the cylinder being perpendicular to the axis of bore 100. This cylindrical surface is so arranged that it intersects the cylindrical bore. This creates two openings 128 located diametrically opposite one another which constitute a connection between chambers 94 and 96 and bore 100 and therefore create the possibility of a connection between measuring cell 32 and chambers 94 and 96.

Openings 128 are sealed by dialytic membranes 130. The latter are pressed by membrane retaining members 132 against the contacting surface 134 formed by the semi-cylindrical wall of the chamber. The side of membrane retaining pieces 132 which abuts membranes 130 is also of cylindrical shape, the radius of curvature being matched to the curvature of surface 134. In the region of bore 128, the membrane retaining members have a recess 136 into which the cell holder 102 project (see FIG. 5). Commercially available dialytic membranes can be used to constitute the above described membranes.

Members 132 are pressed against surface 134 by a clamping arrangement. This arrangement includes a bushing 138 which has an open end fastened to the wall of the housing which faces away from block 98, mounted coaxially with bore 118. The closed end of bushing 138 has a threaded bore 140 in a direction coaxial to its longitudinal axis. A hollow screw 142 may be screwed into bore 140. As shown in FIG. 5, when screw 142 is screwed out of bushing 138, membrane holder 132 is pressed against surface 134 thereby clamping membrane 130 tightly between surface 134 and member 132 to form a tight seal. To allow current to flow between electrodes 122 through measuring cell 32, a through channel 144 is provided in membrane holders 132, the channel being aligned with the inside bores of hollow screw 142 and bushing 138. In order to allow a buffer solution to flow into the through channel, through openings 146 are provided in bushing 138 and the membrane holder. These through openings also allow air to escape which may have been enclosed in the hollow spaces. Turning of the hollow screw can be effected with the aid of a pin which is inserted into radial bores 148 of the screw.

It is a great advantage of the present invention that the test fluid may be replaced without affecting the buffer solution in chambers 94 and 96. Cell holder 102 can even be pushed out of board 100 without allowing buffer fluid to enter the board. Thus the fluid test samples can be exchanged rapidly, again increasing the speed with which a series of measurements can carried out.

The housing is preferably made of acrylic glass. A preferred material for manufacturing cell holder 102 and membrane holder 132 is polytetrafluor ethylene since it is impervious to fluid and slides readily. The measuring cell can be a glass capillary tube of, for example, 0.8 mn inside diameter whose inner surface is coated with, for example, a hydrogel in order to prevent electrosmosis by shielding the charges on the glass walls. The electrodes may consist of a silver/silver chloride electrode pair or a platinum/platinum electrode pair.

Figure 8:
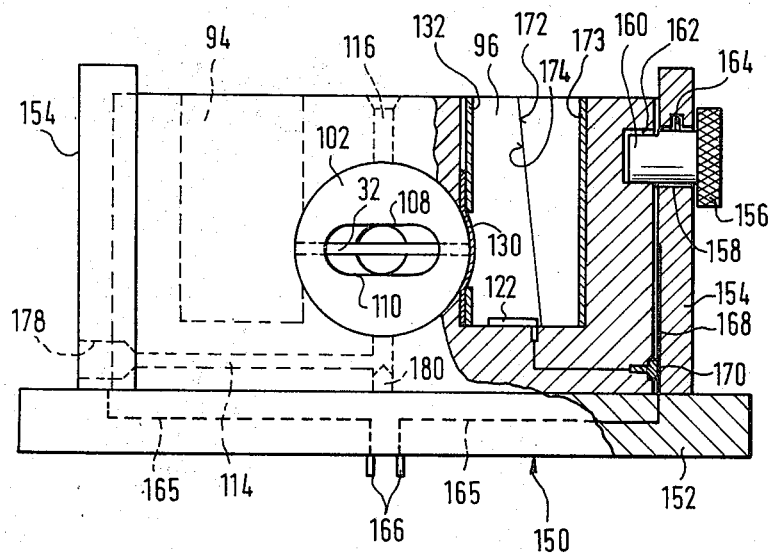
FIG. 8 is a partially sectional side view of an alternate embodiment of the measuring cell.

FIG. 8 shows an alternate embodiment of the measuring cell arrangement, in a partly sectional side view, the same elements again having the same reference numerals.

In the measuring cell arrangement shown in FIG. 8, the blocked-shaped housing 92 is contained within an outer casing generally denoted by reference numeral 150. Casing 150 has a base plate 152 and two lateral guides 154. Base plate 152 may, for example, be fastened to table 64 in the measuring arrangements shown on FIGS. 1 and 7. A horizontal cross sectional view of lateral guides 154 present a substantially C-shaped profile, the distance between the legs of the C being equal to the width of housing 92. Thus, housing 92 may be inserted into the outer casing from the top between the lateral guides 154 as between two tracks and will be retained in a fixed horizontal position by the lateral guides. A check bolt 156 prevents movement of housing 92 in a vertical direction. Check bolt 156 passes through a bore 158 and lateral guide 154 in the right hand side of FIG. 8 and has a free end 160 which engages a substantially circular recess 162 in the side of housing 92 facing lateral guide 154. The position of check bolt 156 shown in FIG. 8 can be fixed by means of a locking pin 164 in a type of bayonet catch arrangement. Turning locking pin 164 through a predetermined angle frees it, allowing check bolt 156 to be pulled out of recess 162. In order to clamp housing 92 fixedly within outer casing 150, the free end 160 of check bolt 156 is eccentric to its axis, the position of the eccentric being such that check bolt 156 abuts the lower portion of recess 162 when in its final position and thereby presses housing 162 against base plate 152.

Conductors 165 are imbedded in base plate 152, for connecting contacts 166 on the bottom of base plate 152 with sliding contacts 168 arranged on the inner side of lateral guides 154. Each side of housing 92 facing a lateral guide 154 has a contact pin 170 which is connected to the electrode 122 projecting into buffer chambers 94 and 96 respectively. Chambers 94 and 96 are each cylindrically shaped. Membrane holder 132 is a half cylinder whose edges 172 are inclined at an angle relative to the cylinder axis. Holder 132 is pressed against the wall of chamber 94 by means of a half cylindrical clamp 174 whose edges 176 are inclined at an angle complementary to the angle of the edges of membrane holder 132. When clamp 174 is inserted into a chamber 96, it acts as a wedge which pushes membrane holder 132 against the membrane.

In the measuring arrangement according to FIG. 8, the inlet channel 114 ends on one side of housing 92, a bore 178 aligned with inlet channel 114 being provided in lateral guide 54, so that, for example, a syringe with the material to be examined can be inserted into inlet channel 114. An opening for cleaning purposes which can be closed by a plug 180 is situated at the intersection of the horizontal part of inlet channel 114 and a vertical rise thereof.

The measuring arrangement shown on FIG. 8 functions in the same way as that shown in FIGS. 5 and 6.

While the invention has been illustrated in preferred embodiments, it is not to be limited to the circuits or structures shown, since many variations thereof will be evident once skilled in the art and are intended to be encompassed in the present invention as set forth in the following claims.

We claim:

1. In apparatus for measuring the velocity in a predetermined direction of particles in a fluid by evaluation of an output signal created by heterodyning of a reference beam of electromagnetic radiation with a scattered beam formed from radiation scattered at a selected one of a plurality of scattering angles by said particles in said fluid, said apparatus comprising a measuring cell, a source of electromagnetic radiation, means for splitting said electromagnetic radiation into a measuring beam and a reference beam and for guiding said measuring beam to impinge upon said measuring cell at a predetermined incident angle, whereby said measuring beam is scattered by said particles at a plurality of scattering angles measured relative to said incident angle, movable selector means for picking up said scattered radiation at each of said selected scattering angles and creating scattered beams corresponding thereto, and means for mixing a first and second beam impinging at a predetermined location upon said mixing means thereby creating a heterodyne signal, the improvement comprising
    means for automatically controlling the direction of propagation of said reference beam and said scattered beams so that said reference beam and said selected one of said scattered beams impinge upon said predetermined location in said mixing means independently of the position of said movable selector means, whereby said mixing means mixes said reference beam with said selected scattering beam thereby creating said output signal without external adjustment of said direction of propagation of said reference beam.

2. Apparatus as set forth in claim 1, wherein said mixing means is mounted in a fixed position;
    wherein said beam splitting means is in a fixed position relative to said mixing means and deviates said reference beam toward said predetermined location in said mixing means; and
    wherein said control means comprises a convex lens positioned between said measuring cell and said mixing means and having a focal point within said measuring cell and an optical axis, whereby said scattered radiation leaves said convex cell in a direction parallel to said optical axis, and means for creating relative movement in a direction perpendicular to said optical axis between said measuring cell and said convex lens on the one hand and said selector means on the other hand.

3. Apparatus as set forth in claim 2, wherein said selector means comprises a right angle deviating prism; and wherein said moving means comprises means for moving said deviating prism in a direction perpendicular to said optical axis of said convex lens selectively away from or toward said mixing means.

4. Apparatus as set forth in claim 3, further comprising a pin diaphragm arranged between said deviating prism and said mixing means.

5. Apparatus as set forth in claim 3, wherein said convex lens constitutes a first convex lens;
further comprising a second convex lens arranged between said beam splitting means and said measuring cell, said second convex lens having a focal point within said measuring cell and having an optical axis.

6. Apparatus as set forth in claim 5, wherein said selector means constitutes first selector means;
further comprising second selector means positioned in the path of said measuring beam between said beam splitting means and said second convex lens; and
wherein said control means further comprises means for moving said second selector means relative to said second convex lens.

7. Apparatus as set forth in claim 6, wherein said first convex lens and said first selector means are, respectively, identical to said second convex lens and said second selector means; and
wherein said second selector means and said second convex lens are arranged with mirror image symmetry to said first selector means and said first convex lens relative to a plane extending in a direction perpendicular to said optical axes of said first and second convex lenses through said focal point.

8. Apparatus as set forth in claim 7, wherein said means for moving said first selector means relative to said first convex lens and said means for moving said second selector means relative to said second convex lens comprise means for jointly moving said first and second selector means relative to said first and second convex lenses.

9. Apparatus as set forth in claim 8, wherein said means for jointly moving said first and second selector means comprises a carriage having said selector means mounted thereon, and fine adjustment means for adjusting the position of said carriage relative to said lenses.

10. Apparatus as set forth in claim 7, wherein said first and second selector means are fixedly mounted; and
wherein said means for moving said first and second selector means relative to said first and second convex lenses, respectively comprises means for jointly moving said first and second convex lens and said measuring cell relative to said first and second selector means.

11. Apparatus as set forth in claim 10, wherein said means for jointly moving said lenses and said measuring cell comprises a carriage having said measuring cell and said convex lenses mounted thereon, and fine adjustment means for controlling the movement of said carriage relative to said selector means.

12. Apparatus as set forth in claim 11, wherein said fine adjustment means comprises calibrated fine adjustment means.

13. Apparatus as set forth in claim 7, wherein said measuring cell is a cylindrical measuring cell having a horizontal cylinder axis; wherein said optical axis of said convex lenses is a horizontal axis extending in a direction perpendicular to said cylinder axis of said measuring cell; and
wherein said particles move within said fluid in a horizontal direction perpendicular to said optical axis of said lenses.

14. Apparatus as set forth in claim 7, wherein said direction of movement of said particles is in a vertical direction;
wherein said measuring cell is a cylindrical cell having a horizontal cylinder axis;
wherein said optical axis of said convex lenses is a horizontal axis extending in the direction perpendicular to said cylinder axis of said measuring cell; and
wherein said control means further comprises means for moving said measuring cell relative to said convex lenses in a vertical direction.

15. Apparatus as set forth in claim 1, further comprising means positioned in the path of said reference beam between said beam splitting means and said mixing means for controlling the intensity of said reference beam.

16. Apparatus as set forth in claim 1, wherein said control means comprises rotatable carrier means having said movable selector means and said mixing means mounted thereon in a fixed relative position to each other, means for rotating said rotatable carrier to said scattering angle, and means for directing said reference beam to the so-rotated mixing means.

17. Apparatus as set forth in claim 16, wherein said means for directing said reference beam to the so-rotated mixing means comprises a flexible wave guide.

18. Apparatus as set forth in claim 17, wherein said flexible wave guide comprises a monomode optical fiber;
further comprising optical means for focusing said reference beam onto said optical fiber.

19. Apparatus as set forth in claim 17, wherein the length of path of said reference beam between said beam splitting means and said beam mixing means is equal to the corresponding length of path of said measuring beam.

20. Apparatus as set forth in claim 16, wherein said means for guiding said measuring beam comprises means for guiding said measuring beam along a predetermined line in a vertical plane containing said axis of rotation;
wherein said directing means for said reference beam comprises means for directing said reference beam along a second line in said vertical plane parallel to said predetermined line;
wherein said rotatable carriage is rotatable over a predetermined total angle of rotation; and
wherein said control means further comprises means located at the intersection of said second line and said axis of rotation for scattering said reference beam over an angular region at least equal to said maximum angle of rotation of said rotatable carriage.

21. Apparatus as set forth in claim 20, wherein said reference beam scattering means comprises a cylindrical glass capillary tube mounted coaxially with said axis of rotation.

22. Apparatus as set forth in claim 20, wherein said reference beam scattering means comprises the tip of a needle mounted coaxially with said axis of rotation.

23. Apparatus as set forth in claim 16, wherein said measuring cell is rotatably mounted about said axis of rotation.

24. Apparatus as set forth in claim 16, further comprising means located in the path of said reference beam for adjusting the intensity thereof.

25. Apparatus as set forth in claim 16, further comprising a table carrying said source of electromagnetic radiation, said beam splitter and said measuring cell;
wherein said rotatable carrier comprises a disk rotatably mounted on said table; and
further comprising angle measuring means for measuring the angle of rotation of said disk.

26. Apparatus as set forth in claim 1, further comprising a housing having an inlet port and an outlet port;
wherein said measuring cell is a tube having a first and second open end;
further comprising cell holder means for holding said cell, said cell holder means being rotatably mounted in said housing for moving said cell from a refill position wherein said first and second open ends are aligned with said inlet and outlet port, respectively, to a measurement position wherein said open ends are sealed from the atmosphere.

27. Apparatus as set forth in claim 26, wherein said housing comprises a block having a cylindrical bore having a predetermined diameter, said inlet port and said outlet port constituting ports arranged diametrally opposite one another in said block; and
wherein said cell holder is a cylindrical body having an outer diameter corresponding to said diameter of said bore in said block, said cylindrical body having a diametral opening for receiving said measuring cell and an axial through channel for allowing passage of said measuring beam.

28. Apparatus as set forth in claim 27, wherein said housing further comprises a first and second chamber arranged on opposite sides of said block, each containing a buffer fluid and an electrode.

29. Apparatus as set forth in claim 28, wherein said bore in said block for holding said cell holder is connected to said first and second chamber through a first and second opening located diametrically opposite one another in said block and set off by a predetermined angle in the circumferential direction relative to said inlet port and said outlet port; and
further comprising membranes sealing said openings relative to said fluids but permitting current to flow between said chambers.

30. Apparatus as set forth in claim 29, wherein said block has a first and second surface respectively adjacent to said first and second chamber;
wherein each of said surfaces has a cylindrical contact surface in the area of said openings, said cylindrical contact surface having a generatrix perpendicular to the axis of said bore receiving said cell holder and intersecting said bore;
further comprising a first and second partially cylindrical membrane holding member having a clamping surface matched to said contact surface and having a through channel aligned with said first and second opening, respectively, and means for clamping said membrane holding member against said contact surface.

31. Apparatus as set forth in claim 30, wherein said clamping means comprises a bushing having an internal thread, and a hollow screw adapted to be screwed into said bushing, said hollow screw having an axially bore; and
wherein said clamping arrangement is braced on the one hand by said membrane holding member and on the other hand by a wall of said chamber.

32. Apparatus as set forth in claim 30, wherein said membrane holding member is a semicylindrical member having edges extending at a predetermined angle to the cylinder axis thereof; and
wherein said clamping means comprises a clamping member having edges complementary to the edges of said membrane holding member.

33. Apparatus as set forth in claim 29, further comprising a first and second electrode holder; and
wherein said electrodes are detachably mounted on said first and second electrode holders.

34. Apparatus as set forth in claim 33, wherein said housing has a first and second threaded bore;
wherein said electrode holders are screwed into said first and second threaded bore, respectively, and carry said first and second electrodes at respective internal extremities extending into said first and second chamber;
further comprising a first and second terminal located outside of said first and second chamber, respectively and, respectively, connected to said first and second electrode.

35. Apparatus as set forth in claim 26, wherein said measuring cell is a glass capillary tube.

36. Apparatus as set forth in claim 27, wherein said opening in said cell holder for receiving said measuring cell has an internal diameter; and
wherein the outer diameter of said measuring cell is slightly larger than said inner diameter.

* * * * *